(12) United States Patent
Rapoport

(10) Patent No.: US 9,448,093 B2
(45) Date of Patent: Sep. 20, 2016

(54) MEASUREMENT OF PROPERTIES OF FLUIDS USING MRI

(71) Applicant: Aspect AI Ltd., Shoham (IL)

(72) Inventor: Uri Rapoport, Moshav Ben Shemen (IL)

(73) Assignee: ASPECT AI LTD., Shoham (IL)

( * ) Notice: Subject to any disclaimer, the term of this patent is extended or adjusted under 35 U.S.C. 154(b) by 373 days.

(21) Appl. No.: 13/939,330

(22) Filed: Jul. 11, 2013

(65) Prior Publication Data

US 2014/0049257 A1  Feb. 20, 2014

Related U.S. Application Data

(60) Provisional application No. 61/683,292, filed on Aug. 15, 2012, provisional application No. 61/684,758, filed on Aug. 19, 2012.

(51) Int. Cl.

| | |
|---|---|
| G01V 3/00 | (2006.01) |
| G01F 1/716 | (2006.01) |
| G01N 24/08 | (2006.01) |
| G01R 33/563 | (2006.01) |
| G01N 11/00 | (2006.01) |

(52) U.S. Cl.
CPC .............. *G01F 1/716* (2013.01); *G01N 24/085* (2013.01); *G01R 33/56308* (2013.01); *G01N 2011/0006* (2013.01); *G01N 2011/0086* (2013.01)

(58) Field of Classification Search
USPC ......................................................... 324/306
See application file for complete search history.

(56) References Cited

U.S. PATENT DOCUMENTS

| | | | |
|---|---|---|---|
| 5,532,593 A | 7/1996 | Maneval et al. | |
| 5,757,187 A | 5/1998 | Wollin | |
| 6,549,007 B1 * | 4/2003 | Hills | G01R 33/44 324/303 |
| 6,856,132 B2 * | 2/2005 | Appel | G01V 3/32 324/303 |
| 7,295,933 B2 | 11/2007 | Gysling et al. | |
| 7,486,071 B2 | 2/2009 | Care et al. | |
| 8,736,263 B2 * | 5/2014 | Minh | G01N 24/081 324/303 |
| 2012/0092007 A1 | 4/2012 | Li et al. | |

* cited by examiner

*Primary Examiner* — Rodney Fuller
(74) *Attorney, Agent, or Firm* — Pearl Cohen Zedek Latzer Baratz LLP

(57) ABSTRACT

A method of determining rheological properties of a fluid. The method includes: providing an open-bore tube and defining within the bore a three dimensional grid (3DG) of voxels; defining at least an inlet cross section (ICS) and an outlet cross section (OCS); defining a volume of interest within the bore between the ICS and the OCS; obtaining rheological properties of the fluid; applying a pressure gradient to the bore between the ICS and the OCS; and nuclear magnetic resonance imaging the fluid within the volume of interest to determine various aspects of the fluid.

16 Claims, 14 Drawing Sheets

Velocity Profiles for Different Types of Fluid
Same Maximum Velocity

MEASUREMENT OF PROPERTIES OF FLUIDS USING MRI

CROSS-REFERENCE TO RELATED APPLICATIONS

This application is a claims the benefit of U.S. Provisional Patent Application No. 61/683,292 filed on Aug. 15, 2012 and the benefit of U.S. Provisional Patent Application No. 61/684,758, filed Aug. 19, 2012, all of which are hereby incorporated by reference.

FIELD OF THE INVENTION

The present invention generally pertains to a system and method for measurement of properties of fluids using MRI.

BACKGROUND OF THE INVENTION

U.S. Pat. No. 5,532,593 to Maneval et al. discloses an apparatus and method for obtaining rheological information about a fluid using nuclear magnetic resonance. A fluid flowing through a tube is subjected to nuclear magnetic resonance imaging signals to obtain the velocity profile of the fluid. The pressure gradient between two points along the tube is also obtained. The shear rate is then determined from the velocity profile, and the shear stress is determined from the pressure gradient. From a single velocity profile, data is obtained over shear rates ranging from zero at the center of the tube to the maximum shear rate at the tube wall. Alternatively, the velocity spectrum can be obtained and used in the same manner. The shear stress versus shear rate curve can thereby be obtained from a single nuclear magnetic resonance image taken at a specific value of the pressure gradient. However, only a radial (2D) velocity profile is taught in U.S. Pat. No. 5,532,593.

U.S. Pat. No. 5,757,187 to Wollin discloses a device and a method wherein weak oscillating gradients are used to modulate the angular momentum of the spins in a magnetic resonance imaging apparatus producing output signals in the receiver coil which can be synchronously demodulated to yield a periodic envelope containing integral harmonics of the oscillating gradient frequency. This periodic envelope is subjected to synchronous detection, continuously yielding the amplitudes of the individual harmonic components of the envelope which are then used to approximate an integral equation by a matrix solution to a linear transformation which generates the Radon transform of the transverse magnetization along the direction of the oscillating gradient, permitting image reconstruction. Truncation (Gibbs) artefacts are eliminated. Synchronous demodulation and synchronous detection of the impulse spectrum of the output signal from the receiver coil suppresses the continuous spectrum Johnson noise. The very weak higher harmonics are synchronously detected over multiple periods yielding an improved estimate of their central tendency. However, Wollin teaches a method of measuring a radial (2D) velocity profile and Wollin does not teach a method of deriving rheological parameters from the velocity data.

It is therefore a long felt need to provide a system and method for obtaining rheological information about a flowing fluid that is not limited to radial (2D) measurements.

SUMMARY OF THE INVENTION

It is an object of the present invention to disclose a system for measurement of properties of fluids using MRI. It is another object of the present invention to disclose a method for determining flow characteristics of a flowing fluid in a tube, comprising steps of: Providing a system for determining flow characteristics of a flowing fluid in a tube comprising: an NMR device configured to produce at least one image of the flowing fluid, the NMR device at least partially surrounding the tube; and a processor configured to create at least one 3D velocity image of the flowing fluid from the at least one image of the flowing fluid; Flowing the fluid through the tube; and Creating the at least one 3D velocity image of the flowing fluid. From the least one 3D velocity image of the flowing fluid is determined at least one of a group consisting of fluid material characteristics, existence of fluid material inhomogeneities, presence of laminar flow and presence of turbulent flow.

It is another object of the present invention to disclose the method, comprising an additional step of measuring pressure of the fluid at a plurality of points along the tube and determining pressure gradients in the fluid from the measured pressures.

It is another object of the present invention to disclose the method, comprising an additional step of converting the pressure gradient to 3D shear stress values for the fluid.

It is another object of the present invention to disclose the method, comprising an additional step of converting the 3D velocity profile to 3D shear rate values for the fluid.

It is another object of the present invention to disclose the method, comprising an additional step of determining a shear stress-shear rate curve for the fluid at the applied pressure gradient.

It is another object of the present invention to disclose the method, comprising an additional step of determining rheological characteristics of the fluid in 3D from analysis of the at least one 3D velocity image using the shear stress-shear rate curve for the fluid.

It is another object of the present invention to disclose the method, comprising an additional step of selecting the rheological characteristics from a group consisting of fluid type, fluid density, fluid viscosity, fluid yield stress, exponent n, and constant K.

It is another object of the present invention to disclose the method, comprising an additional step of selecting the fluid type from a group consisting of Newtonian fluid, pseudoplastic fluid, dilatant fluid, Bingham plastic fluid, and Herschel-Bulkley fluid.

It is another object of the present invention to disclose the method, comprising an additional step of selecting the inhomogeneities in the fluid from a group consisting of gas bubbles, liquid bubbles, stratification, settlement, brokendown emulsion, and incomplete mixing.

It is another object of the present invention to disclose the method, comprising an additional step of identifying regions of turbulence by irregularities in the shape of the flow front.

It is another object of the present invention to disclose the method, comprising an additional step of identifying regions of turbulence by the presence of eddies in the velocity field.

It is another object of the present invention to disclose the method, further comprising a step of displaying the 3D velocity image on a display device.

It is another object of the present invention to disclose a system for determining flow characteristics of a flowing fluid in a tube, comprising: an NMR device configured to produce at least one image of the flowing fluid, the NMR device at least partially surrounding the tube; and a processor configured to create at least one 3D velocity image of the flowing fluid from the at least one image of the flowing fluid. From the least one 3D velocity image of the flowing fluid is determined at least one of a group consisting of fluid material characteristics, existence of fluid material inhomogeneities, presence of laminar flow and presence of turbulent flow.

It is another object of the present invention to disclose the system, wherein pressure of the fluid is measured at a plurality of points along the tube and pressure gradients in the fluid are determined from the measured pressures.

It is another object of the present invention to disclose the system, wherein the pressure gradient is converted to 3D shear stress values for the fluid.

It is another object of the present invention to disclose the system, wherein the 3D velocity profile are converted to 3D shear rate values for the fluid.

It is another object of the present invention to disclose the system, wherein a shear stress-shear rate curve is determined for the fluid at the applied pressure gradient.

It is an object of the present invention to disclose the system, wherein rheological characteristics of the fluid are determined in 3D from analysis of the at least one 3D velocity image using the shear stress-shear rate curve for the fluid.

It is another object of the present invention to disclose the system, wherein aid rheological characteristics are selected from a group consisting of fluid type, fluid density, fluid viscosity, fluid yield stress, exponent n, and constant K.

It is another object of the present invention to disclose the system, wherein the fluid type is selected from a group consisting of Newtonian fluid, pseudoplastic fluid, dilatant fluid, Bingham plastic fluid, and Herschel-Bulkley fluid.

It is another object of the present invention to disclose the system, wherein the inhomogeneities in the fluid are selected from a group consisting of gas bubbles, liquid bubbles, stratification, settlement, broken-down emulsion, and incomplete mixing.

It is another object of the present invention to disclose the system, wherein regions of turbulence are identified by irregularities in the shape of the flow front.

It is still another object of the present invention to disclose the system, wherein regions of turbulence are identified by the presence of eddies in the velocity field.

It is another object of the present invention to disclose the system, wherein the 3D velocity image is displayed on a display device.

BRIEF DESCRIPTION OF THE FIGURES

In order to better understand the invention and its implementation in practice, a plurality of embodiments will now be described, by way of non-limiting example only, with reference to the accompanying drawings, wherein FIG. 1 schematically illustrates velocity profiles for different types of fluid.

DETAILED DESCRIPTION OF THE PREFERRED EMBODIMENTS

Figure 1:
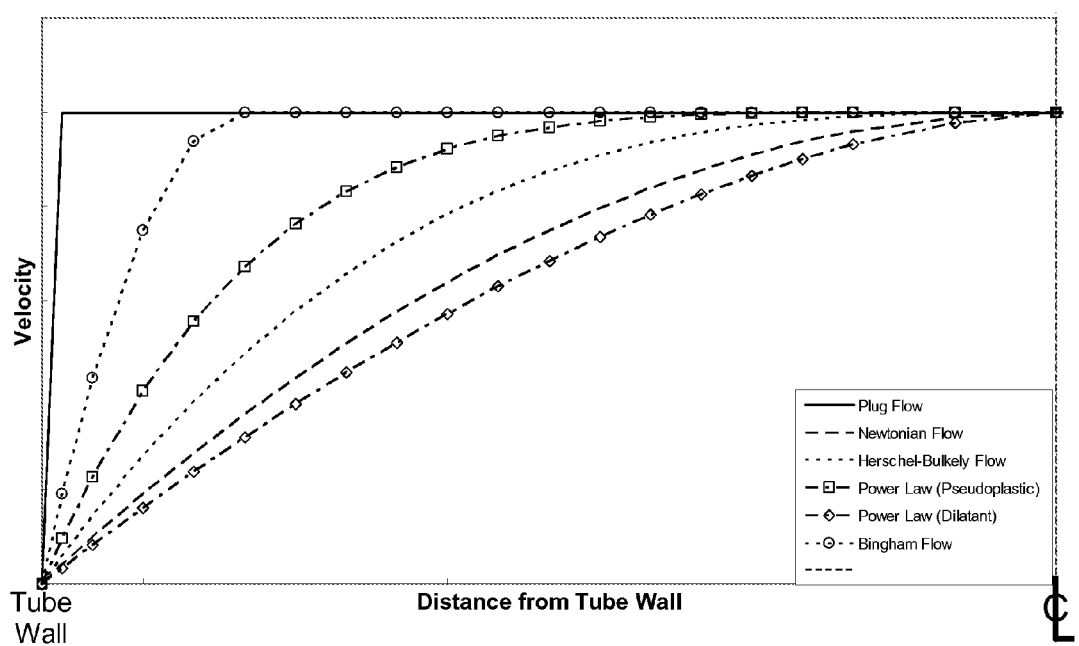

The following description is provided, alongside all chapters of the present invention, so as to enable any person skilled in the art to make use of the invention and sets forth the best modes contemplated by the inventor of carrying out this invention. Various modifications, however, will remain apparent to those skilled in the art, since the generic principles of the present invention have been defined specifically to provide a means and method for measurement of properties of fluids using MRI.

The term 'bubble' hereinafter refers to a region substantially filled with a fluid of with characteristics which differ significantly from those of the main body of the flowing fluid. Bubbles need not be substantially spherical or ovoid, but the fluid therein should be of relatively uniform quality. A non-limiting example of a bubble is a region of air larger than approximately a millimeter within an emulsion or a liquid. Other non-limiting examples of bubbles are a region of oil within an emulsion or a liquid, or a region of liquid within a gas.

The terms 'about' and 'approximately' hereinafter refer to + or −25% of a value.

The system of the present invention uses 3D NMR to determine 3D velocity profiles of a flowing fluid and to determine rheological parameters from the 3D velocity profiles.

There are several advantages to 3D velocity profiles over 2 D profiles. 2D profiles, because of their two dimensional nature, can only give a velocity profile through one slice of the flowing fluid. For example, if the slice is perpendicular to the predominant direction of flow of the fluid (such as a slice parallel to the cross-section of a pipe through which the fluid is flowing), the velocity profile can be determined for that cross-section of the pipe. Such a velocity profile can determine asymmetries in the velocity profile for locations in that cross section. Such asymmetries can indicate, for example, as discussed hereinbelow, bubbles in the fluid. However, such a two-dimensional slice can not distinguish between a small, local bubble and the permanent presence of gas in the pipe. A vertical, longitudinal section could determine whether there was a layer of gas overlying other fluids in the pipe, for example if the pipe were underfilled, but could not identify bubbles away from the central, vertical diameter of the slice, bubbles which would be identifiable in a horizontal longitudinal slice. A series of cross-sectional slices at a fixed location could identify such an overlying layer of gas, but the time to identify the problem would be limited by the flow velocity of the fluid. In contrast, a 3D velocity profile can be used to identify rheological parameters and variations in them at any position within the 3D volume of interest and identification of both longitudinal and cross-sectional variation is not limited by the flow velocity of the fluid.

In an embodiment of the invention, the flowing fluid is in a plug reactor; the NMR device at least partially surrounds at least a portion of the plug reactor. The velocity profile measured by the NMR device is used to characterize the flowing material. The results of the characterization can be used to control the reaction, including such aspects as altering the composition of the fluid, altering the temperature profile of the fluid, altering mixing of the fluid or any of its components, by any of stirrers, shakers or rotators, irradiating the fluid (visible light sources, sources of IR electromagnetic radiation, sources of UV electromagnetic radiation, x-ray sources, sources of microwave radiation and ultrasound sources) and stopping, starting or aborting at least a portion of the reaction. The reaction control mechanism can be upstream, in conjunction with, or downstream of the NMR device.

Figure 2:
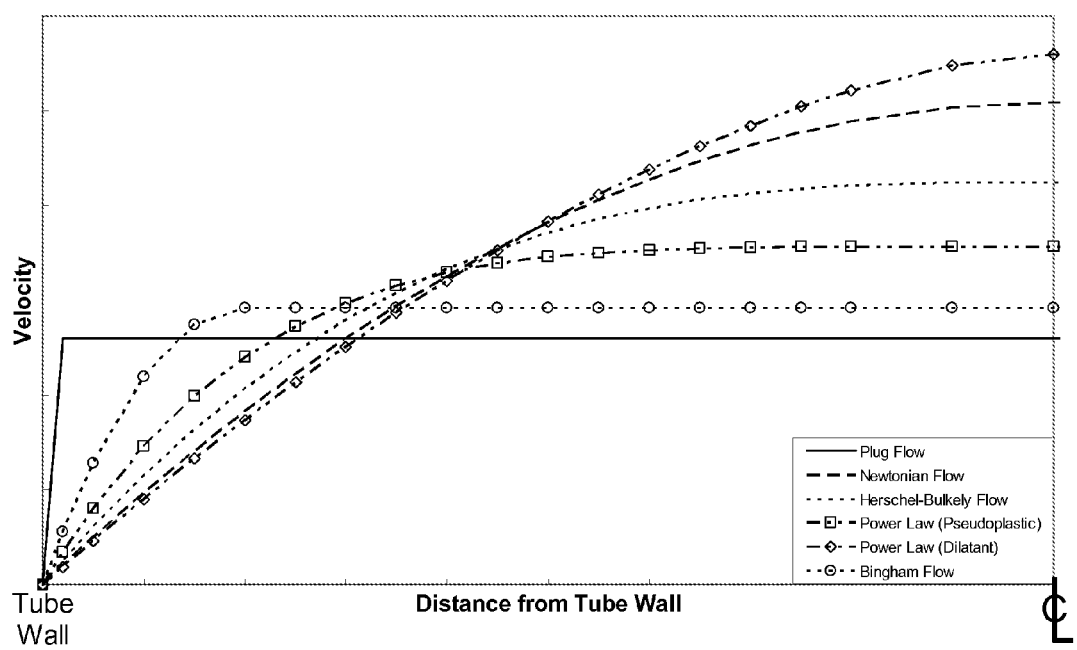
FIG. 2 schematically illustrates velocity profiles for different types of fluid.

Fluids can be characterized by the shape of the flow profile. FIG. 1 illustrates schematically the shapes of flow profiles for different types of fluids, normalized to the same maximum flow velocity. FIG. 2 illustrates the same flow profiles, normalized to the same total flow rate. It is clear that the type of flow exhibited by the fluid can easily be determined from the flow profiles. Furthermore, as described hereinbelow, characteristics of the fluid such as viscosity can be determined from the flow profile.

Figure 3:
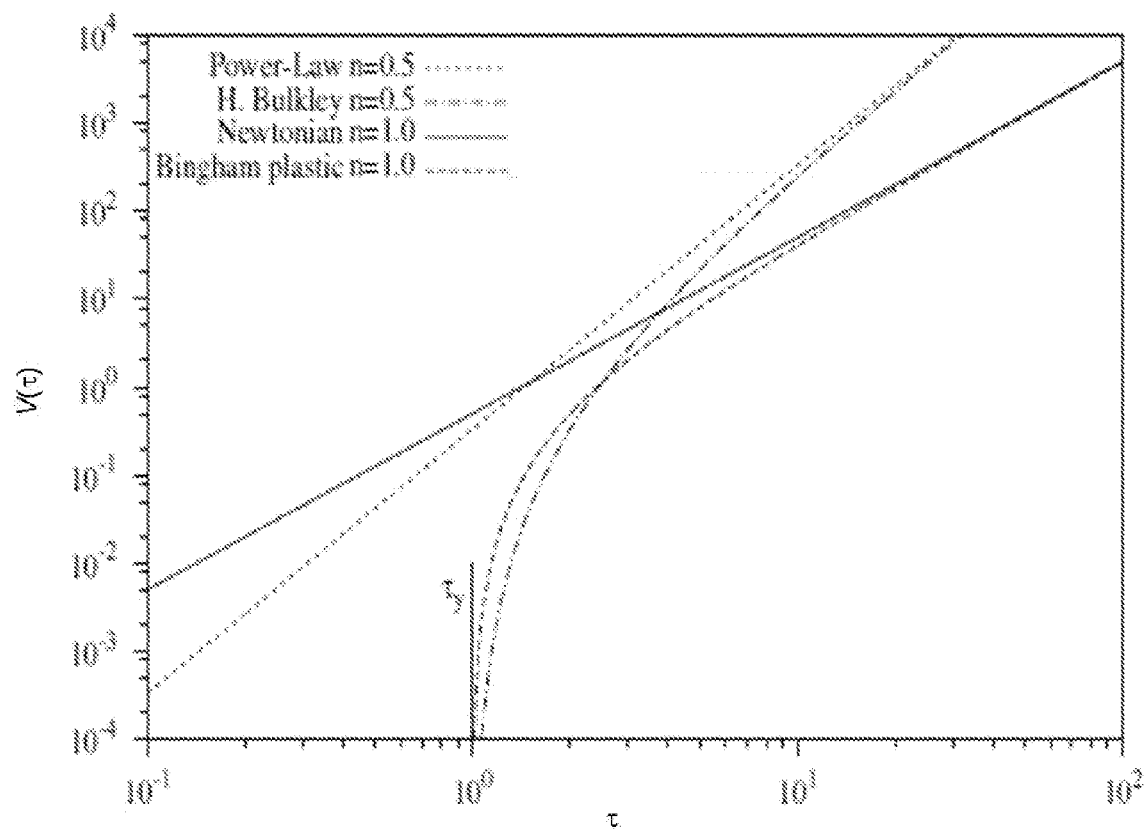
FIG. 3 schematically illustrates the rescaled velocity as a function of shear stress for different types of fluid.

FIG. 3 schematically illustrates how the shear stress depends on velocity gradient for different types of fluid. For the Newtonian fluid, the shear stress increases linearly with velocity gradient; the slope of the curve, the viscosity of the fluid, is constant. Bingham plastic fluids also have constant slope, but if the shear stress is less than a minimum value, $\tau_0$, the velocity will be zero—the material acts like a solid for shear stresses less than $\tau_0$. For pseudoplastic fluids, the slope, the viscosity, decreases with increasing velocity gradient, and for dilatant fluids, the viscosity increases with increasing velocity gradient.

Figure 4:
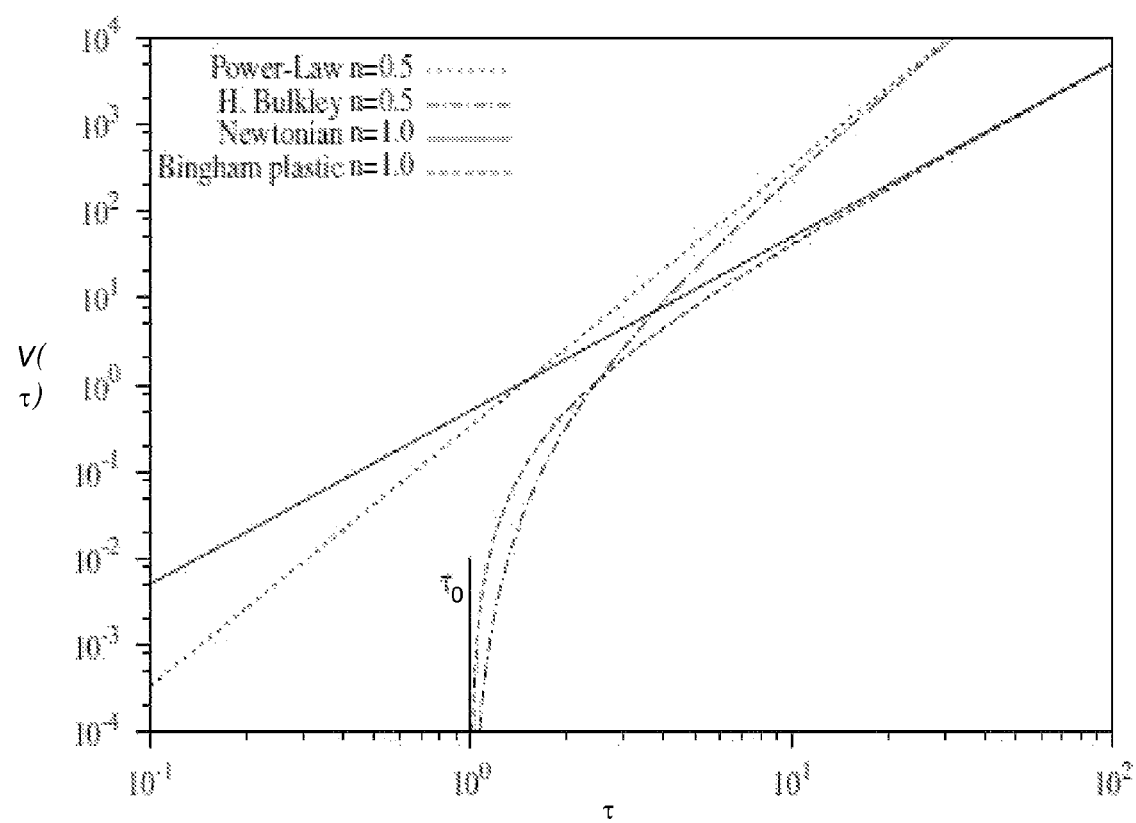
FIG. 4 schematically illustrates the velocity gradient as a function of shear stress.

FIG. 4 illustrates a log-log plot of how the rescaled velocity depends on shear stress for different types of fluid. For the Newtonian fluid, the curve is a straight line with slope 1; the exponent n=1. For pseudoplastic fluids (power law fluids with n<1), the curve is a straight line with slope 1/n, so the slope is greater than 1. Herschel-Bulkley and Bingham plastic fluids both have a stress $\tau_0$ below which the material acts like a solid. For shear stresses below that value, the velocity is zero. For stresses significantly greater than $\tau_0$, a Bingham plastic behaves like a Newtonian fluid, a Herschel-Bulkley fluid like a power-law fluid.

Measuring velocity profiles directly from NMR images suffers badly from the effects of noise in the NMR signal. However, the extraction of velocity profiles can be made more robust by the use of velocity rescaling techniques. In one embodiment of a rescaling technique, a rescaled velocity dependent on the shear stress is used. The shear stress in the fluid inside a circular pipe, $\tau(r)$, as a function of radius r is $$\tau(r) = \frac{\Delta P}{2L} r$$

Where $\Delta P$ is the pressure drop in the pipe and L is the length of the pipe. Since $\tau(r)$ is a linear function of r, velocity as a function of the shear stress, $v=v(\tau)$ can be used instead of the more usual $v=v(r)$. Then a rescaled velocity $V(\tau)$ can be defined as $$V(\tau) \equiv |v(0) - v(\tau)| \frac{\Delta P}{2L} \tag{1}$$

This function is zero at the center of the tube, where $v(\tau)=v(0)$ and is nowhere negative. The derivative of the rescaled velocity is $$\frac{dV}{d\tau} = \frac{dv(\tau)}{d\tau} \frac{\Delta P}{2L} \tag{2}$$

And since $$\frac{dV}{d\tau} = \frac{dv(r)}{dr} \frac{dr}{d\tau} = \dot{\gamma} \frac{2L}{\Delta P} \tag{3}$$

The derivative $dV/d\tau$ is the shear rate $$\frac{dV(\tau)}{dr} = \dot{\gamma} \tag{4}$$

The function $V(\tau)$ can therefore also be found by integrating equation (4), $$V(\tau) = \int_0^\tau \frac{dV(\tau)}{\tau} d\tau = \int_0^\tau \dot{\gamma}(\tau) d\tau \tag{5}$$

From equation (6), it is clear that the function $V(\tau)$ depends only on the shear strain rate $\dot{\gamma}$, so that no fitting or smoothing of the data is required in order to find the velocity profile. The shear stress t can be written as a function of the shear strain rate $\dot{\gamma}$ as $$\tau = \tau_y + K|\dot{\gamma}|^n \quad \tau > \tau_y \tag{6}$$

where $\tau_y$ is the yield stress, and K and n are constants characterizing the fluid. Values of $\tau_y$, K and n for different types of fluid are shown in Table 1, where $\eta$ is the viscosity of the fluid.

TABLE 1

| Type of Fluid | Yield stress $\tau_y$ | Exponent n | Constant K |
| --- | --- | --- | --- |
| Newtonian | 0 | 1 | $\eta$ |
| Power law (pseudoplastic) | 0 | <1 | $\eta$ |
| Power law (dilatant) | 0 | >1 | $\eta$ |
| Bingham | >0 | 1 | K |
| Herschel-Bulkley | >0 | ≠1 | K |

Solving eq. (6) for $\dot{\gamma}$, $$\dot{\gamma} = \left(\frac{\tau - \tau_y}{K}\right)^{\frac{1}{n}} \tag{7}$$

Inserting eq. (7) into eq. (5), the rescaled velocity $V(\tau)$ is $$V(\tau) = \begin{cases} \int_{\tau_y}^\tau \left(\frac{\tau - \tau_y}{K}\right)^{\frac{1}{n}} d\tau = \frac{(\tau - \tau_y)^{\frac{n+1}{n}}}{\frac{n+1}{n} K^{\frac{1}{n}}} & \tau > \tau_y \\ 0 & \tau \leq \tau_y \end{cases} \tag{8}$$

FIG. 3 illustrates the effect of the parameters K, n, and $\tau_y$ on $V(\tau)$. In FIG. 3, $V(\tau)$ is plotted as a function of $\tau$ on a log-log plot, for which $$\ln V(\tau) = \frac{n+1}{n} \ln(\tau - \tau_y) - \ln\left(\frac{n+1}{n} K^{\frac{1}{n}}\right) \tag{9}$$

Eq. 9 will be a straight line if $\tau_y=0$, i.e., for power law fluids and for Newtonian fluids. For power law fluids, n=1 so that the slope is 2. Newtonian fluids of differing viscosities will be vertically displaced by ln(2η), with lines of high viscosity below lines of low viscosity. Power law fluids with n<1 (pseudoplastic fluids) will have slopes greater than 2, while power law fluids with n>1 (dilatant fluids) will have slopes between 1 and 2, with the slope approaching 1 as n increases.

Fluids with non-zero yield stress will have a linear region where $\tau \gg \tau_y$, but the slope will rapidly approach infinity as $\tau$ approaches $\tau_y$. For the Newtonian case, where n=1, solving equation (8) for the viscosity η and equation (7) for the strain rate $\dot{\gamma}$ give $$\eta = \frac{\tau^2}{2V(\tau)} = \frac{\Delta P^2}{2L|v_0 - v|} \qquad (10)$$

and $$\dot{\gamma} = \frac{2V(\tau)}{\tau}$$

The function $f(\tau) = \tau^2/(2V(\tau)) = \Delta P^2/(2L|v_0-v|)$ is also useful for non-Newtonian fluids. If equation (8) is inserted into equation (10), the function f(τ) becomes $$f(\tau) = \frac{n+1}{2n} K^{\frac{1}{n}} \tau^2 (\tau - \tau_y)^{-\frac{n+1}{n}} \qquad (11)$$

Taking the log of both sides of eq. (11), $$\ln(f(\tau)) = \ln\left(\frac{n+1}{2n} K^{\frac{1}{n}}\right) + 2\ln\tau - \frac{n+1}{n} \ln(\tau - \tau_y) \qquad (12)$$

And, if the yield stress $\tau_y = 0$, $$f(\tau) = \frac{n+1}{2n} K^{\frac{1}{n}} \tau^{\frac{n-1}{n}} \qquad (13)$$

Taking the log of both sides of eq. (13), $$\ln(f(\tau)) = \ln\left(\frac{n+1}{2n} K^{\frac{1}{n}}\right) + \frac{n-1}{n} \ln(\tau) \qquad (14)$$

Which is a straight line of slope (2n−1)/n and intercept $$\ln\left(\frac{n+1}{2n} K^{\frac{1}{n}}\right).$$

Since the viscosity as a function of shear stress for the abovementioned fluids takes the form $$\eta(r) = \tau \left(\frac{\tau - \tau_y}{K}\right)^{-\frac{1}{n}} \qquad (15)$$

The ratio of f(τ)/η(τ) becomes $$\frac{f(\tau)}{\eta(\tau)} = \frac{n+1}{n} \frac{\tau}{\tau - \tau_y} \qquad (16)$$

So that f(τ) can be easily determined from η(τ), as n can be found from plots of ln(f(τ)) versus ln(τ) or of ln(V(τ)) versus ln(τ).

In NMR imaging systems, the velocity of material flowing through an envelope such as a tube or conduit can be found using either time of flight techniques or using phase encoding techniques. In either case, the flowing fluid is exposed to a constant magnetic field of a known strength, with a known spatial variation. After the spin systems have aligned with the imposed magnetic field, they are disturbed by a radio-frequency pulse that tags a region in the flow. Time of flight techniques involve building a velocity image by successively exciting a particular cross-section of the flow and detecting the arrival of the excited spins downstream from where they were excited. By knowing the downstream location where the spins were detected and the time between excitation and detection, the velocity profile can be constructed for laminar, unidirectional flow. Phase encode imaging produces direct images of velocity profile distributions for both unidirectional and more complex flows. In the case of unidirectional, steady flow, if the position of a nucleus with spin at time t is z(t), then $z(t)=z_0+wt$ where $z_0$ is the position of the nucleus with spin at time zero and w is the velocity of the nucleus with spin. The applied magnetic field gradient in the flow direction has magnitude $g_z$ and the Bloch equations show that the phase of the magnetization is given by $$\phi = \gamma_g \int_0^t z(s) g_z(s) ds = \gamma(z_0 m_0 + w m_1) \qquad (17)$$

where $\gamma_g$ is the gyromagnetic ratio of the nucleus and $$m_0 = \int_0^t g_z(s) ds$$

$$m_1 = \int_0^t s g_z(s) ds \qquad (18)$$

In phase encode imaging, the applied gradient is designed such that $m_0=0$ but $m_1 \neq 0$. Then the phase angle is proportional to the velocity of the nucleus with spin; a properly designed gradient allows the phase to measure the distribution of velocities in the sample.

In an embodiment of the system of the present invention, gradients are chosen such that a three-dimensional map of the fluid front is generated from the velocity as a function of position in the sample.

In another embodiment of the system of the present invention, three 2D images of the flow front are created, each image perpendicular to the other two, and a 3D image of the flow front is recreated from the three images.

In other embodiments, more than three 2D images are created, and the angles between at least some of them differ from 90°. For a non-limiting example, an image is created perpendicular to the direction of the flow, and three further images are made, all three perpendicular to the first one and each of the further images at 60° to the other two further images.

From the velocity distribution and the pressure drop across the sample, the rescaled velocity V(τ) (eq. (8)) is found. Using either eq. (9) or eq. (12), the type of flow can be found from the slope and the constant K from the intercept. From these, the viscosity, η, of the fluid can be found.

Figure 5:
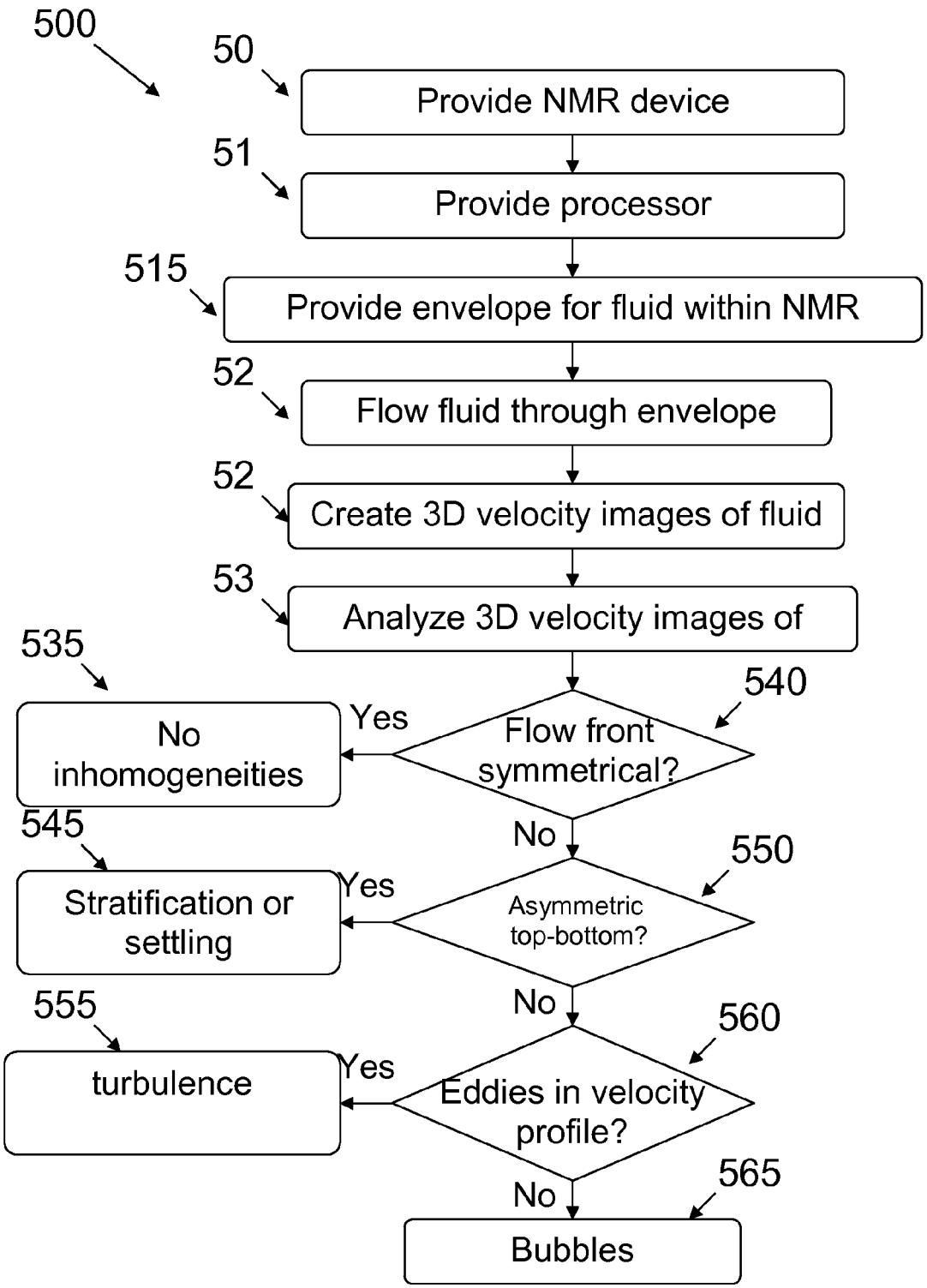
FIG. 5 illustrates an embodiment of a method of determining fluid inhomogeneities.

FIG. 5 illustrates an embodiment of a method (500) by which inhomogeneities in the flow can be found. An NMR device (505) and processor (510) are provided. A fluid envelope is provided (515), preferably a tube or conduit, at least partially enclosing the fluid and at least part of the envelope carrying fluid through the magnetic field of the NMR device. Fluid is caused to flow through the envelope and through the NMR device (520), and 3D velocity images are created of the flowing fluid (525), using any of the methods known in the art. From the 3D velocity image, a flow front is determined (530), using any of the techniques known in the art. If the flow front is symmetrical (540), there are no inhomogeneities (535). If the flow front is not symmetrical, the nature of the inhomogeneity is determined. If the flow front shows top-bottom asymmetry (550), with the profile showing left-right symmetry but not top-bottom symmetry, then stratification or settling has occurred (545). If the flow is asymmetric, but there is no clear plane of symmetry, then, if eddies exist in the velocity (560), there is turbulence. If there are no eddies, the flow is laminar but there exist bubbles or other inhomogeneities in the fluid.

Figure 6A:
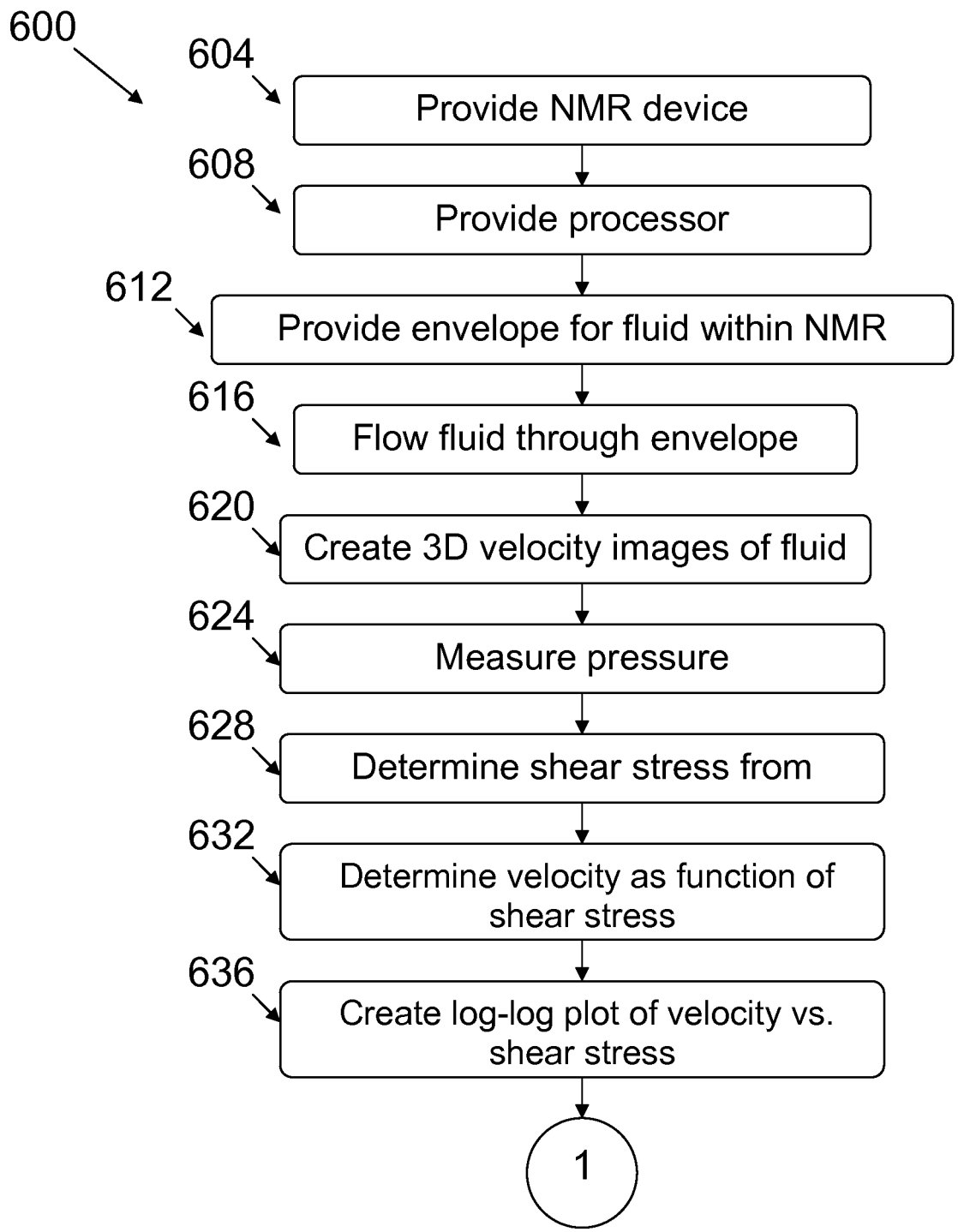
FIGS. 6A and 6B illustrate an embodiment of a method of determining rheological parameters of a fluid.
Figure 6B:
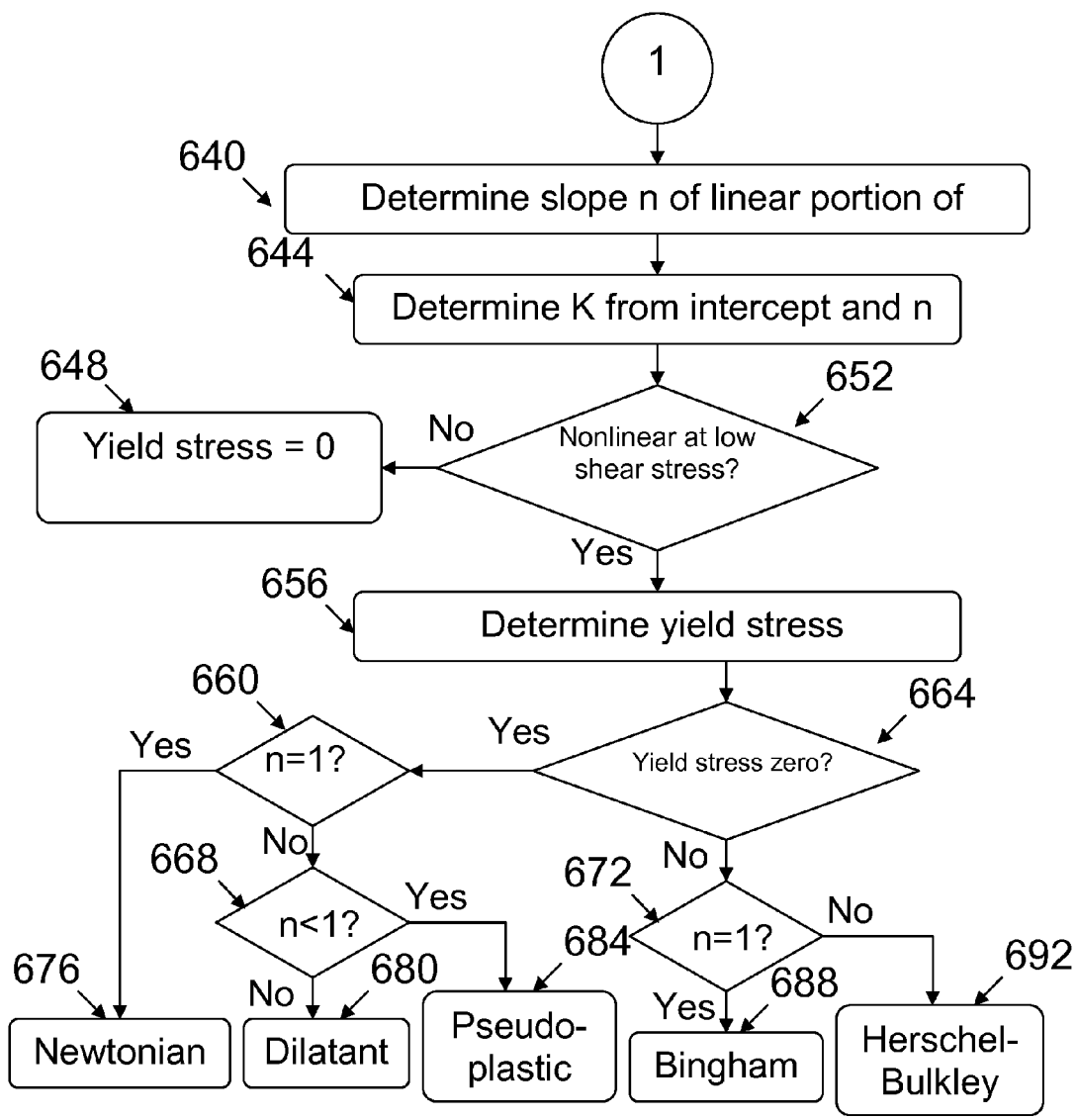

FIGS. 6A and 6B illustrate a method of determining the rheological parameters of the fluid from the flow profile. An NMR device (604) and processor (608) are provided. A fluid envelope is provided (612), preferably a tube or conduit, at least partially enclosing the fluid and at least part of the envelope carrying fluid through the magnetic field of the NMR device. Fluid is caused to flow through the envelope and through the NMR device (616), and 3D velocity images are created of the flowing fluid (620), using any of the methods known in the art. The pressure in the fluid is measured (624), preferably at several points along the envelope. The shear stress is determined as a function of position from the pressure gradients and the position (628), using the equation $$\tau(r) = \frac{\Delta P}{2L} r.$$

The velocity is determined as a function of shear stress and the rescaled velocity is calculated (632) and a log-log plot of the rescaled velocity as a function of shear stress is created (636). The linear portion of the curve can be determined (640), using any of the methods known in the art, and the slope of the linear portion, n, calculated, using any of the methods known in the art. Once the slope n has been found, the constant K can be calculated (644) from the intercept of the linear portion with the shear stress $\tau=0$ axis, where K=

$$K = \left[\left(\frac{n}{n+1}\right)\exp(-\text{Intercept})\right]^n.$$

If the curve remains linear even for the lowest shear stresses, (652), then the yield stress is zero (648). Otherwise, the yield stress (656) is found from the value of $\tau$ where the rescaled velocity decreases rapidly.

With the yield stress, n, and K, the type of fluid can be determined. If the yield stress is zero (664) and n=1 (660), then the flow is Newtonian (676) and K is the viscosity, $\eta$. If the yield stress is zero (664) and n<1 (668), then the flow is pseudoplastic (684). Otherwise, n>1 and the flow is dilatant (680). If the yield stress is nonzero (664) and n=1 (672) then there is Bingham flow. Otherwise, the flow is Herschel-Bulkley flow (692). Since all the parameters for the flow have been determined, the flow is completely rheologically characterized. This characterization can be done in 3D, so that rheological differences between different regions in the flow can be determined. From the data, the flow front can be plotted. In some embodiments, the shape of the flow front is used to characterize the fluid. For non-limiting example, asymmetries in the flow front can indicate the presence of gas bubbles in the fluid, incomplete mixing of the components, unstable flow, or breakdown of an emulsion. The shape of the flow front can also be used to distinguish between laminar and turbulent flow, with turbulent flow having a flatter profile than laminar flow.

In one embodiment, the reaction is occurring during the time that the fluid is within the NMR device. The shape of the flow front, as described hereinabove, will characterize the maturity of the reaction so that corrective feedback can be applied, for example by altering the temperature of the tube walls, to bring the maturity within the desired parameters.

Figure 7:
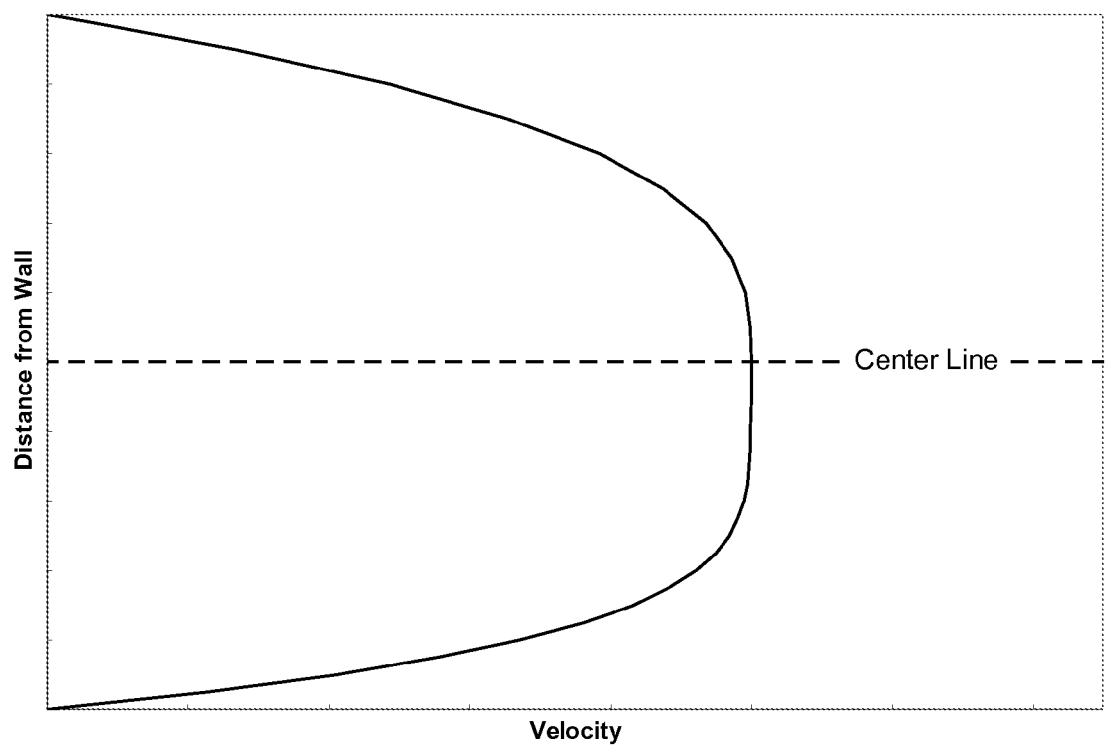
FIG. 7 illustrates an example of flow with top-bottom asymmetry.

In another embodiment, the product is an emulsion such as mayonnaise. Emulsions normally exhibit Herschel-Bulkley type flow, with a sharply-pointed flow profile. If air bubbles are present or if the emulsion is breaking down, the flow profile becomes less pointed. Air bubbles or bubbles of unemulsified fluid will also cause asymmetries in the flow front, as will settlement of one or more components out of the emulsion. FIG. 7 illustrates an example of a flow front where settlement has occurred.

In other embodiments, the system incorporates feedback mechanisms such that, if at least one rheological property of the fluid does not satisfy at least one desired criterion, at least one production parameter for the process is altered so as to cause the at least one rheological parameter of the fluid to satisfy the at least one desired criterion.

In yet another embodiment, the NMR system incorporates both high magnetic field NMR and low magnetic field NMR, such that a high resolution image of the velocities is acquired with the high-field system, a high-contrast image of the velocities is acquired with the low-field system, and the two images are fused to provide a high-contrast, high resolution image of the flow front of the fluid.

Example 1

Figure 8A:
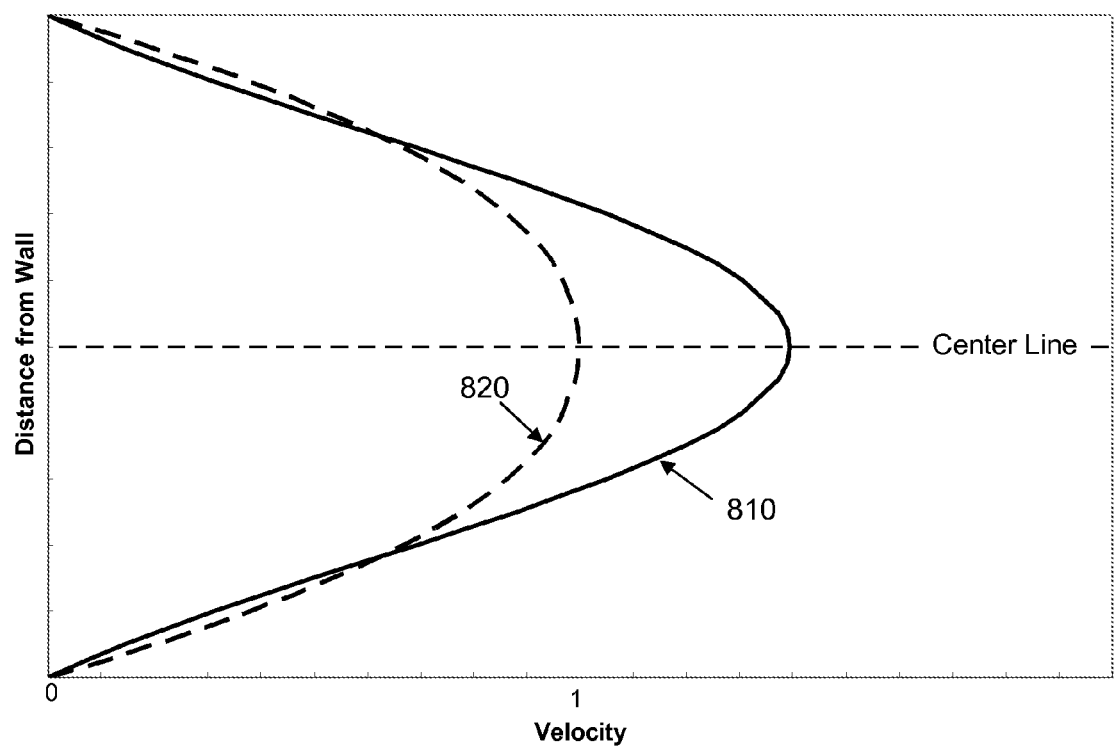
FIGS. 8A-C illustrate a comparison of rheological properties of flows with different flow exponents n.

Comparison Between Power Law Exponent in a Flowing Fluid and Power Law Exponent Stored in a Database FIG. 8A illustrates in a non limiting manner and in an out of scale fashion a 2D slice through a flow front, showing the velocity as a function of position across the tube. The solid line (810) shows the actual velocity, while the dashed line (820) shows the expected velocity for the material, as stored in a database.

Figure 8B:
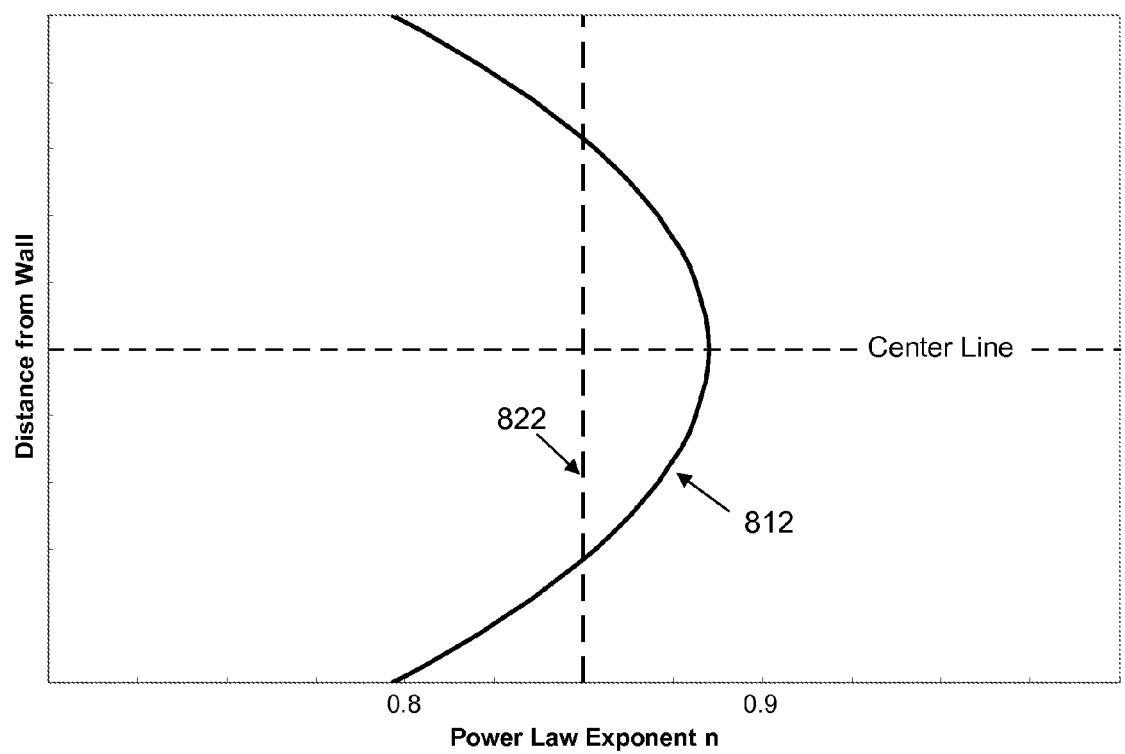
Figure 8C:
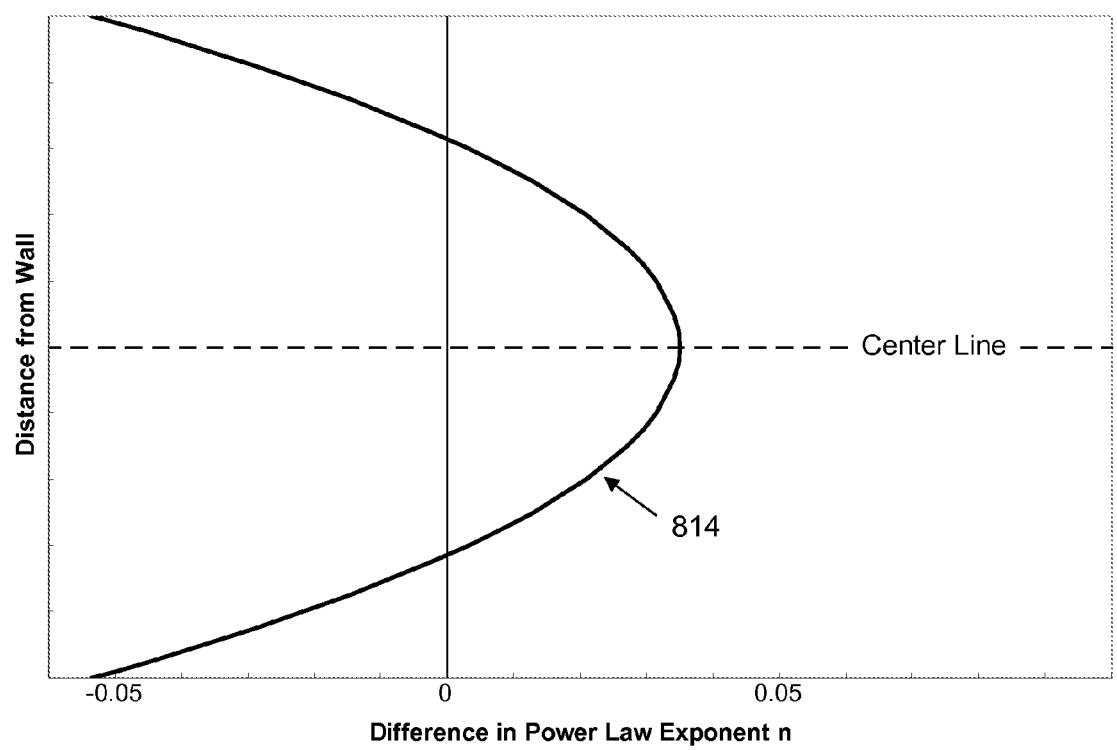

FIG. 8B depicts a graph of the power law exponent n as a function of position across the tube, as derived from the velocity curves and the pressure data, as described hereinabove. The exponent n is a constant, 0.85, for the stored database fluid (822). It averages about 0.85 for the actual fluid (812), but varies from about 0.89 near the center of the tube to about 0.8 at the edges of the tube. FIG. 8C plots the difference, showing clearly that the fluid is more Newtonian than the standard in the database at the center of the tube, but less so at the edges.

Example 1I

Figure 9A:
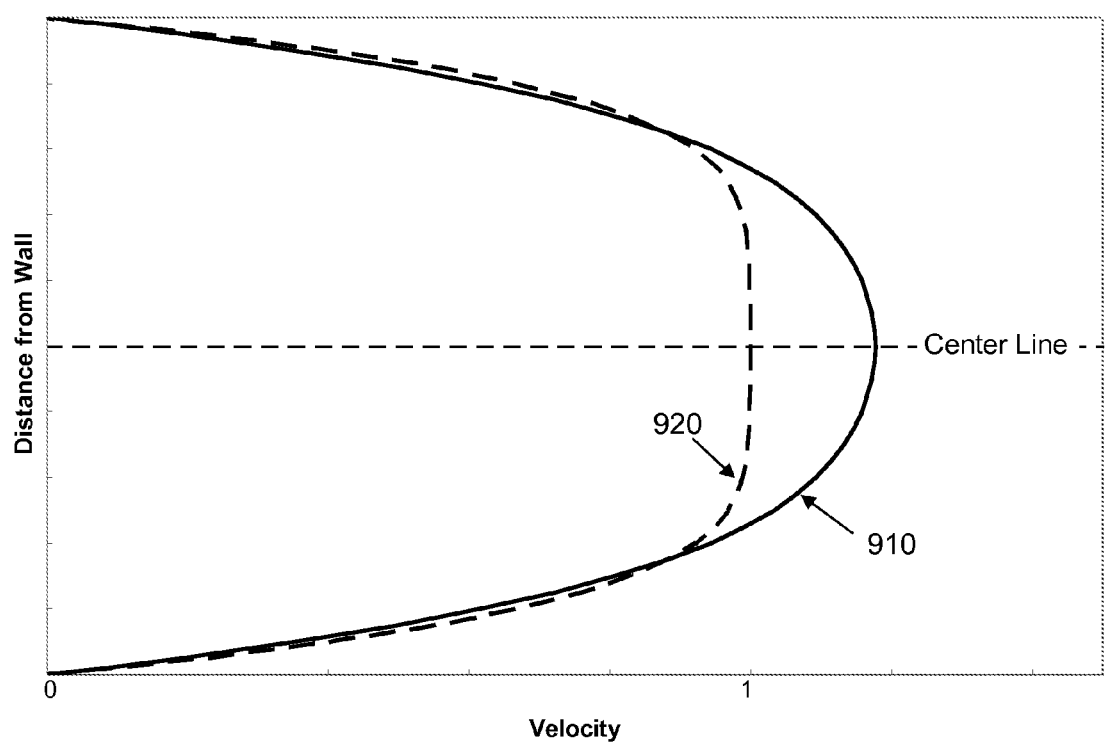
FIGS. 9A-C illustrate a comparison of rheological properties of flows with different viscosities η.

Comparison Between Viscosity in a Flowing Fluid and Viscosity Stored in a Database FIG. 9A illustrates, still in a non limiting manner and in an out of scale fashion, a 2D slice through a flow front, showing the velocity as a function of position across the tube. The solid line (910) shows the actual velocity, while the dashed line (920) shows the expected velocity for the material, as stored in a database.

Figure 9B:
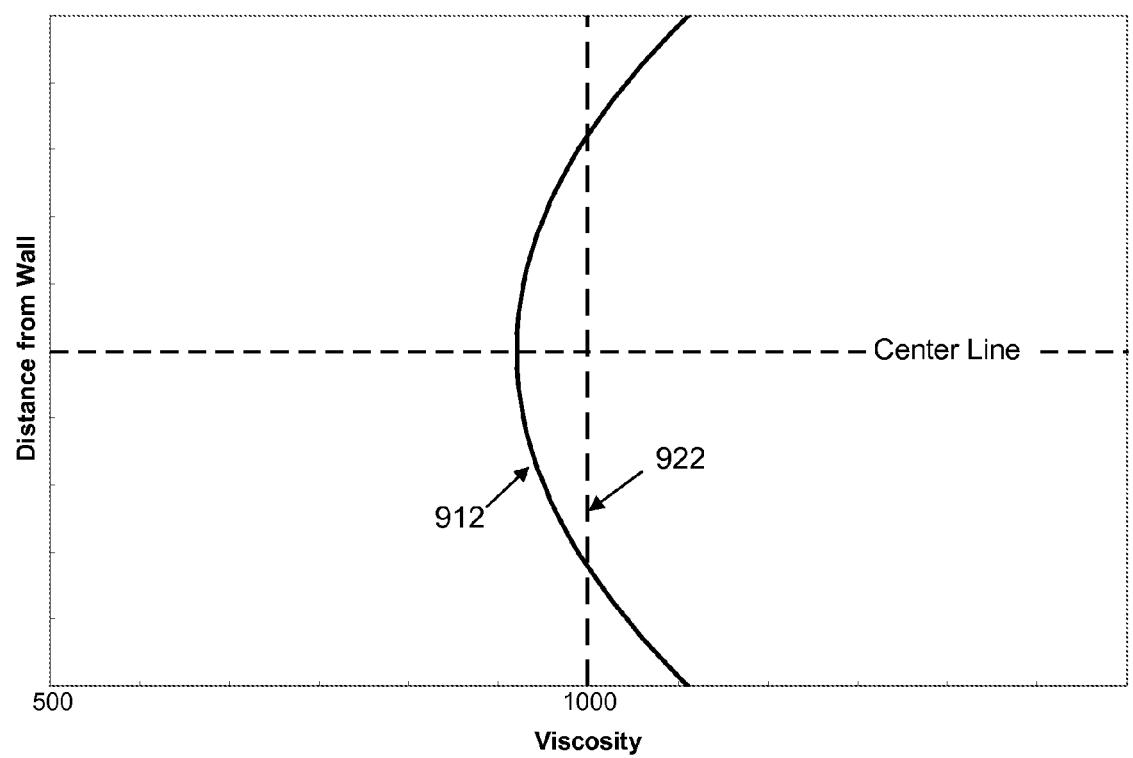
Figure 9C:
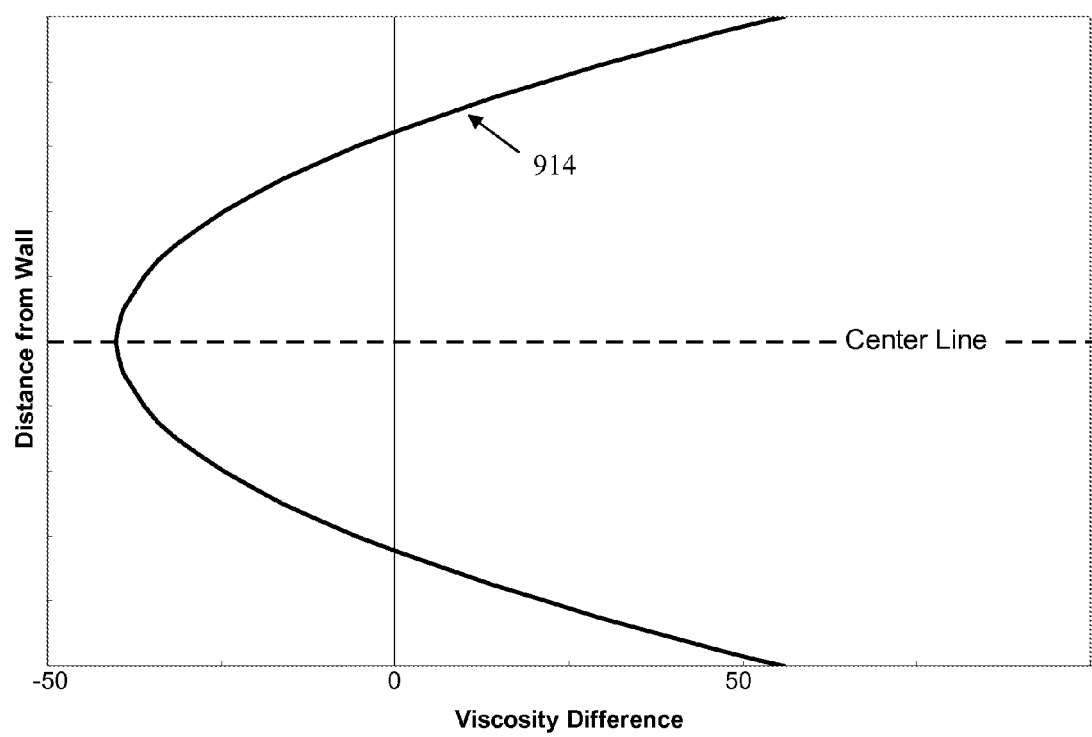

FIG. 9B depicts a graph of the viscosity as a function of position across the tube, as derived from the velocity curves and the pressure data, as described hereinabove. The viscosity is a constant, 1000, for the stored database fluid (922). It averages about 1000 for the actual fluid (912), but varies from about 960 near the center of the tube to about 1060 at the edges of the tube. FIG. 9C plots the difference, showing clearly the deviations from the desired constant viscosity of the fluid in the tube.

The invention claimed is:

1. A method for determining rheological properties of a fluid, comprising the steps of:
   a. providing an open-bore tube and defining within said bore a three dimensional grid (3DG) of voxels, with each voxel $Vox_i$ having a position $(x_i, y_i, z_i)$ in said 3DG; defining at least two different cross sections, namely inlet cross section (ICS) and outlet cross section (OCS); and defining a volume of interest (VOI) within said bore between said ICS and said OCS;
   b. obtaining a database of rheological properties of said fluid;
   c. applying a pressure gradient to said bore between said ICS and said OCS, thereby flowing said fluid through said tube;
   d. NMR imaging said fluid within said VOI, said image having a plurality p of slices, each slice comprising a plane within said 3DG;
   e. from said image, for each of said voxels $Vox_i$, determining a velocity for said fluid $v_i$;
   f. for each of said voxels $Vox_i$, from said velocity $v_i$, calculating shear rate values (SRV); whilst, before or after determining a pressure gradient between said at least one ICS and said at least one OCS and thereby calculating shear stress values (SSV) for each voxel $Vox_i$, from said SRV and said SSV determining at least one rheological property $RP_i$ for each voxel $Vox_i$;
   g. comparing, for said at least one rheological property, $RP_i$ calculated for voxel $Vox_i$ to stored $RP_i$ for voxel $Vox_i$ from said database, thereby determining the difference in rheological property $DRP_i$ for voxel $Vox_i$; and
   h. from the set of said $DRP_i$, calculating 3D variations in said rheological property, therefrom determining the difference in rheological property $DRP_i$ as a function of position $(x_i, y_i, z_i)$ in said grid;
   wherein the resolution of said difference in rheological property $DRP_i$ is multiplied by about p compared to the per-slice resolution.

2. The method of claim 1, comprising an additional step of selecting said rheological properties from a group consisting of fluid type, fluid density, fluid viscosity, fluid yield stress, and any combination thereof.

3. The method of claim 1, comprising an additional step of selecting said fluid type from a group consisting of Newtonian fluid, pseudoplastic fluid, dilatant fluid, Bingham plastic fluid, and Herschel-Bulkley fluid.

4. The method of claim 1, comprising an additional step of identifying inhomogeneous regions in said fluid.

5. The method of claim 4, wherein said inhomogeneous regions in said fluid are selected from a group consisting of gas bubbles, liquid bubbles, regions of stratification, regions of settlement, regions of broken-down emulsion, and regions of incomplete mixing.

6. The method of claim 1, comprising an additional step of identifying regions of turbulence by irregularities in the shape of the flow front.

7. The method of claim 1, comprising an additional step of identifying regions of turbulence by the presence of eddies in the velocity field.

8. The method of claim 1, further comprising a step of displaying said 3D velocity image on a display device.

9. A method for determining rheological properties of a fluid flowing through a tube, comprising the steps of:
   a. providing an open-bore tube and defining within said bore a three dimensional grid (3DG) of voxels, with each voxel $Vox_i$ having a position $(x_i, y_i, z_i)$ in said 3DG;
   defining at least two different cross sections, namely inlet cross section (ICS) and outlet cross section (OCS); and defining a volume of interest (VOI) within said bore between said ICS and said OCS;
   b. applying a pressure gradient to said bore between said ICS and said OCS, thereby flowing said fluid through said tube;
   c. NMR imaging said fluid within said VOI, said NMR image having a plurality p of slices, each slice comprising a plane within said 3DG;
   d. from said image, for each of said voxels $Vox_i$; determining a velocity for said fluid $v_i$;
   e. for each of said voxels $Vox_i$, from said velocity $v_i$, calculating shear rate values (SRV); whilst, before or after determining a pressure gradient between said at least one ICS and said at least one OCS and thereby calculating shear stress values (SSV) for each voxel $Vox_i$, from said SRV and said SSV determining at least one rheological property $RP_i$ for each voxel $Vox_i$;
   f. creating at least two sets of voxels, set $\{Vox_A\}$ comprising at least one voxel $Vox_{A,i}$ and set $\{Vox_B\}$ comprising at least one voxel $Vox_{B,i}$, locations of voxels in set $\{Vox_A\}$ differing from locations of voxels in set $\{Vox_B\}$ in a systematic way, each voxel $Vox_{A,i}$ in set $\{Vox_A\}$ having a corresponding voxel $Vox_{B,i}$ in set $\{Vox_B\}$;
   g. comparing, for said at least one rheological property, for said at least two sets of voxels, rheological property $RP_{A,i}$ for each voxel $Vox_{A,i}$ in set $\{Vox_A\}$ to rheological parameter $RP_{B,j}$ for corresponding voxel $Vox_{B,j}$ in set $\{Vox_B\}$ thereby determining differences in rheological property $DRP_{ij}$ at relative position $(x_k, y_k, z_k)$; and
   h. from the set of said $DRP_{ij}$, calculating 3D variations in said rheological property, therefrom determining the relative difference in rheological property $DRP_{ij}$ as a function of relative position $(x_k, y_k, z_k)$ in said grid
   wherein the resolution of said difference in rheological property $DRP_{ij}$ is multiplied by about p compared to the per-slice resolution.

10. The method of claim 9, comprising an additional step of selecting said rheological properties from a group consisting of fluid type, fluid density, fluid viscosity, fluid yield stress, and any combination thereof.

11. The method of claim 9, comprising an additional step of selecting said fluid type from a group consisting of Newtonian fluid, pseudoplastic fluid, dilatant fluid, Bingham plastic fluid, and Herschel-Bulkley fluid.

12. The method of claim 9, comprising an additional step of identifying inhomogeneous regions in said fluid.

13. The method of claim 12, wherein said inhomogeneous regions in said fluid are selected from a group consisting of gas bubbles, liquid bubbles, regions of stratification, regions of settlement, regions of broken-down emulsion, and regions of incomplete mixing.

14. The method of claim 9, comprising an additional step of identifying regions of turbulence by irregularities in the shape of the flow front.

15. The method of claim 9, comprising an additional step of identifying regions of turbulence by the presence of eddies in the velocity field.

16. The method of claim 9, further comprising a step of displaying said 3D velocity image on a display device.

\* \* \* \* \*